(12) United States Patent
Dolez et al.

(10) Patent No.: US 12,571,753 B2
(45) Date of Patent: Mar. 10, 2026

(54) END-OF-LIFE SENSORS FOR FABRICS

(71) Applicant: THE GOVERNORS OF THE UNIVERSITY OF ALBERTA, Edmonton (CA)

(72) Inventors: Patricia Dolez, Edmonton (CA); Hyun-Joong Chung, Edmonton (CA); Chungyeon Cho, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 232 days.

(21) Appl. No.: 18/279,669

(22) PCT Filed: Mar. 3, 2022

(86) PCT No.: PCT/CA2022/000006
§ 371 (c)(1),
(2) Date: Sep. 1, 2023

(87) PCT Pub. No.: WO2022/183272
PCT Pub. Date: Sep. 9, 2022

(65) Prior Publication Data
US 2024/0133835 A1 Apr. 25, 2024
US 2024/0230572 A9 Jul. 11, 2024

Related U.S. Application Data

(60) Provisional application No. 63/156,143, filed on Mar. 3, 2021.

(51) Int. Cl.
*G01N 27/20* (2006.01)
*G01N 33/36* (2006.01)

(52) U.S. Cl.
CPC ........... *G01N 27/20* (2013.01); *G01N 33/367* (2013.01)

(58) Field of Classification Search
CPC ............................ G01N 27/20; G01N 33/367
(Continued)

(56) References Cited

U.S. PATENT DOCUMENTS 5,528,155 A * 6/1996 King .................... G01N 33/442
156/64
6,408,256 B1 * 6/2002 Hittle ..................... G01N 25/18
702/132
(Continued)

OTHER PUBLICATIONS

Paul, Gordon, et al. "An investigation into the durability of screen-printed conductive tracks on textiles." Measurement Science and Technology 25.2 (2014): 025006. (Year: 2014).*
(Continued)

*Primary Examiner* — Christopher P McAndrew
(74) *Attorney, Agent, or Firm* — FIELD LLP; Shohini Bagchee

(57) ABSTRACT

A sensor for measuring the degradation of a fabric property is disclosed. The sensor includes a conductive track and a sacrificial material coupled to the conductive track, such that degradation of the sacrificial material results in reduction or loss of electrical conductivity of the conductive track. A method of measuring the performance degradation of a fabric, using a sensor is also provided. The method includes the step of measuring the electrical resistance of the sensor, and comparing the result to a known or empirically measured value to estimate the remaining useful life of the fabric performance.

30 Claims, 13 Drawing Sheets

(58) Field of Classification Search
     USPC ......................................................... 324/77.1
     See application file for complete search history.

(56)                     References Cited

U.S. PATENT DOCUMENTS

| | | | |
|---|---|---|---|
| 8,981,018 B2 * | 3/2015 | Goldfine ............ | G05D 23/1931 |
| | | | 324/228 |
| 2005/0171703 A1 * | 8/2005 | Goldfine ............ | G01N 27/9013 |
| | | | 702/30 |
| 2006/0077524 A1 * | 4/2006 | Palmateer ............ | G09G 3/3466 |
| | | | 359/291 |
| 2011/0227565 A1 * | 9/2011 | Morton .................... | G01N 3/56 |
| | | | 324/225 |
| 2013/0014873 A1 * | 1/2013 | Voss .................... | B60C 11/0309 |
| | | | 152/209.1 |
| 2014/0147671 A1 * | 5/2014 | Vaz ........................ | D06M 11/83 |
| | | | 428/389 |
| 2015/0084614 A1 * | 3/2015 | Alatainio ................ | G01M 3/16 |
| | | | 324/71.1 |
| 2020/0232904 A1 * | 7/2020 | Wendeler-Goeggelmann ............ | |
| | | | G01N 17/04 |

OTHER PUBLICATIONS

Dolez et al., Advanced Characterization and Testing of Textiles, The Textile Institute Book Series, Jan. 1, 2017, 476 pages, Woodhead Publishing, Cambridge, Massachusetts, United States.

* cited by examiner

Laser engraving

Carbon adhesive
deposition to contact
copper strip and LIG layer

Spin coating
polyimide encapsulant
(non-photosensitive)

END-OF-LIFE SENSORS FOR FABRICS

FIELD OF THE DISCLOSURE

The present disclosure relates generally to devices and methods to monitor stresses that result in loss of performance of specialty fabrics.

BACKGROUND OF THE DISCLOSURE

High-performance or specialty fabrics have been developed for specific uses. In particular, fire protective fabrics have high mechanical performance and are resistant to chemicals, fire and high temperatures.

It is known that while high-performance fabrics, such as those worn by firefighters as protective wear, exhibit exceptional performance when new, their properties may be affected in the long-term as a result of conditions encountered in service, including exposure to temperatures between 100 and 190° C. and heat fluxes between 5 and 10 kW/m² recorded during in-building firefighting training, UV exposure during operations and storage in a lighted space, moisture from external water sources and the firefighter's perspiration and laundering.

A series of testing campaigns performed on used firefighter protective garments, some retired and some not, revealed significant losses of some performance of the clothing. A critical safety concern is that these performance losses sometimes occur before any sign of damage is visible to the naked eye. Since no non-destructive technique is currently available to assess the residual performance of the materials in service, workers at risk of heat and flame exposure have no way of knowing if their clothing is still able to protect them from the hazards associated with their tasks without having it destructively tested, which would make it useless.

The situation has become even more critical following the discovery that smoke particles and combustion-generated carcinogenic chemicals can penetrate firefighters' protective clothing. Since 2010, firefighting has been listed by the World Health Organization as an occupation linked to possible carcinogenic risk. Recent discussions at the National Fire Protection Association (NFPA) led to the proposal of washing protective clothing after each operation to remove fire-generated contaminants from the fabrics. These more frequent launderings will further increase the clothing degradation rate.

There remains a need in the art for non-destructive testing methods for determining remaining useful life, or end-of-life, of high-performance fabrics.

SUMMARY OF THE DISCLOSURE

Generally, the present disclosure relates to sensors for determining a property of a fabric, which property is indicative of remaining useful life of fabric performance.

In general terms, embodiments of a sensor comprise a conductive track produced by layering a conductive material, such as graphene, with compounds that are sensitive to at least one aging condition of a fabric, such as heat, ultraviolet light (UV), and moisture. The compounds may comprise sacrificial polymers, layered onto the conductive material. Upon reaching a certain level of exposure to one of these aging conditions sufficient to cause the performance of the fabric to enter an unsafe range, the compound degrades, causing a rupture in the conductive track. Different or separate conductive tracks may be used to measure the effect of different aging conditions. The measurement of the electrical conductivity of the conductive tracks corresponding to the different aging conditions may then be conducted to determine useful life remaining, if any. This may be part of the regular assessment that workers at risk of heat and flame exposure are required to do of their protective equipment.

A substrate is used to prepare a sensor patch that can be fixed on the garment to monitor its aging condition. This substrate, which can be a fabric, should allow a good coating quality for the conductive material and sacrificial polymer layer(s). For example, the fabric substrate characteristics can have an influence on the coating efficiency by graphene. In addition, the substrate should not interfere with the function of the sensor over its service life. It is thus preferred to optimize the characteristics of the substrate based on the requirements of the application, i.e., the coating process and the service conditions.

UV radiation is a source of degradation, and thus an aging condition, for fabrics used in fire-protective clothing and other types of fabrics. It can originate from exposure to the sun when the clothing is worn outdoors; UV aging may also occur if the clothing is stored in a lighted area. A UV sensor may comprise a UV-sensitive polymer coated on the conductive track, which is in turn formed on the fabric substrate. The UV-sensitive polymer is preferably water, heat, and flame resistant. In some embodiments, a layer of wavelength-shifting polymer may be used to adjust the degradation rate of the sensor to the level of sensitivity of each fabric by shifting the wavelength of the incident radiation to either accelerate or decelerate the photo-degradation of the UV-sensitive polymer.

Thermo-oxidation is another degradation mechanism of fire protective fabrics. It is of importance because of the elevated temperature conditions experienced by the clothing when in operation and during laundering. In the case of volunteer firefighters, keeping their protective gear in a vehicle, which becomes overheated in the summer, may aggravate the situation. A temperature sensor may comprise a temperature-sensitive polymer deposited on the fabric substrate and covered by the conductive track. Preferably a top layer of flame, heat, and water-resistant polymer is used to cover the assembly. Heat resistant in this context is used to means that the assembly will not be affected by high temperature. The thickness of the heat-sensitive polymer layer can serve to adjust the degradation rate of the sensor to the appropriate level of sensitivity for each fabric.

Moisture is another aging condition. Sources of exposure to moisture include liquid water used as an extinguish medium, steam, rain and snow, washing, and the clothing wearer's perspiration. With the current trend towards increased laundering frequency of firefighter protective clothing due to concerns about through-clothing exposure to fire-related contaminants, the effect of laundering on the useful life of protective clothing is of prime importance. While most types of materials used in fire protective fabrics are relatively resistant to water, they may be sensitive to hydrolysis. For example, para-aramid fibres, which are one of the most extensively used materials in fire protective clothing, are very sensitive to hydrolysis. A moisture or hydrolytic sensor may comprise a configuration similar to a UV sensor, i.e., with a moisture-sensitive polymer layer covering the conductive track deposited on the substrate fabric. The polymer thickness will control the response rate of the sensor.

Patches comprising the sensor or sensors may be attached at strategic locations on the protective garment and can undergo all the aging-accelerating events, such as firefighting and washing, that the protective garment fabric experiences. Routinely scheduled measurement of the electrical conductivity of the sensor tracks will be conducted to detect the effect of aging agents on the garments, as part of the regular assessment that workers are required to do of their fire protective equipment.

Thus, in one aspect, the disclosure may comprise a sensor for measuring degradation of a high-performance fabric property, comprising:

(a) a conductive track disposed on a substrate; and
(b) a sacrificial material coupled to the conductive track, such that degradation of the sacrificial material results in reduction or loss of electrical conductivity of the conductive track.

The conductive track can be positioned above or below the layer of sacrificial material.

In another aspect, the disclosure comprises a method of measuring performance degradation of a high-performance fabric, using a sensor as described herein, comprising the step of measuring the electrical conductivity of the sensor, and comparing the result to a known or empirically measured value to estimate the remaining useful life of the fabric performance.

BRIEF DESCRIPTION OF THE FIGURES

The accompanying drawings, which are incorporated herein and form a part of the specification, illustrate some, but not the only or exclusive, examples of embodiments and/or features.

DETAILED DESCRIPTION OF EMBODIMENTS OF THE DISCLOSURE

Definitions. Any term or expression not expressly defined herein shall have its commonly accepted definition understood by a person skilled in the art.

As used herein, the term "fabric" shall mean flexible 2D or 3D textile materials. A textile is made by interlocking yarns, filaments, or fibres, which may be of natural or synthetic origin. Woven fabrics are produced by interlacing two or more yarns perpendicularly to each other. Nonwoven fabrics may comprise a sheet or web comprising entangled fibres, which may be bonded by a mechanical, thermal or chemical process. Different types of finishes may be applied. Fabrics are typically but not necessarily porous.

A high-performance or specialty fabric is one that is formed from a material which either (a) inherently has a protective property, or (b) is treated or modified to have a protective property, which protective property gives the fabric a protective function when worn or used by a user. For example, fire-resistant fabrics may be formed from inherently thermal- and fire-resistant fibres such as para- and meta-aramids.

The sensors of the present disclosure comprise a conductive track. The conductive track may comprise a carbon-based conductive material such as graphene. Other types of suitable conductive materials include metals.

Graphene is well-suited to flexible electronic applications and can be used as the conductive material for the conductive tracks used in the sensors of the present disclosure. As described herein, conductive tracks can be produced by applying the graphene along with compounds that are sensitive to aging conditions of fabrics. Upon reaching a level of exposure to aging-causing agents that is sufficient to cause the fabric to enter an unsafe performance range, the compound will degrade, causing a rupture in the graphene conductive track. The sensor may then be used to signal when the high-performance fabric has become unsafe to use.

The disclosure is described further in reference to fire protective clothing worn by firefighters, however, it may be applied and used in other domains such as, for example, military or industrial safety garments to monitor fabric wear and loss in performance. For example, this may include the transportation industry with seat covers.

The graphene conductive layers are applied in conjunction with one or more other materials that are sensitive to the aging condition for which the sensor is intended to monitor. This sacrificial material preferably comprises a polymer known to degrade with exposure to the aging condition.

Figure 1:
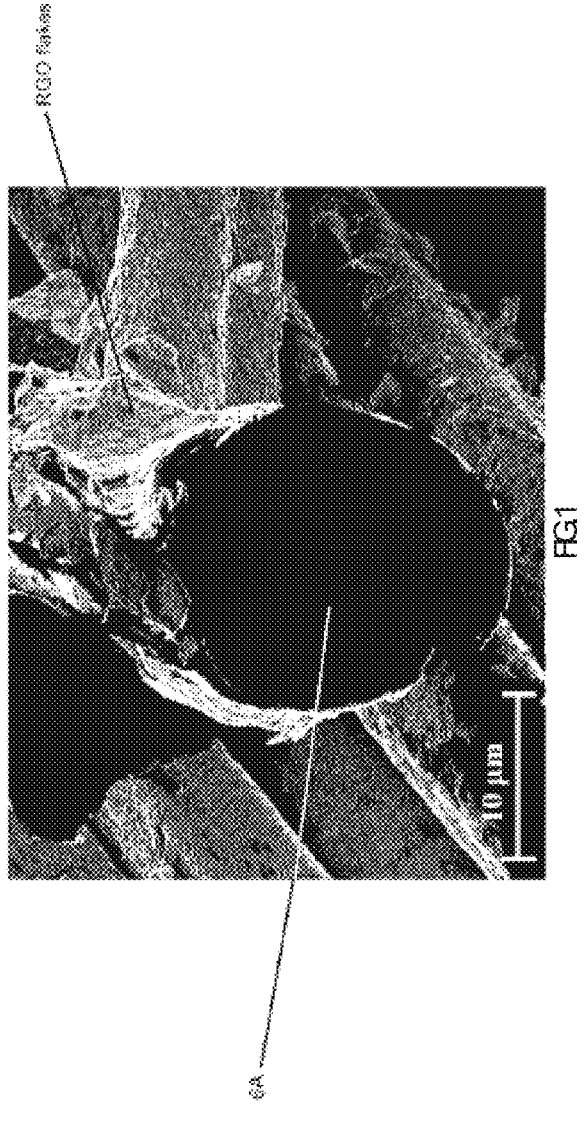
FIG. 1 is a helium ion microscopy image of reduced graphene oxide (RGO) flakes wrapped around individual substrate fibres.

In some embodiments, the graphene conductive tracks may be produced by wrapping self-assembled reduced graphene oxide (RGO) on the substrate. This technique enables wrapping of the self-assembled RGO around and encasing each fiber of the substrate, to achieve electrical conductivity, as shown in FIG. 1. It would be understood that other means of coating in addition to wrapping can also be used to achieve the sensors of the present disclosure, some techniques which are discussed in more detail below. Examples of the coating process include, and are not limited to, spin coating, knife coating, jet printing, layer-by-layer deposition, thermal and/or electron-beam induced atomic/molecular evaporation, sputtering, atomic layer deposition (ALD), surface grafting of polymers, sol-gel deposition, self-assembly, and solution dipping.

All coatings eventually lose their functionality by mechanical wear, chemical degradation, and other operating conditions that cause aging; and the electrical conductivity of an RGO coating is no exception. While such aging-induced loss is a mere nuisance that limits product reliability in most applications, it is used in the present disclosure as the main mechanism for end-of-life forecasting.

One aspect of the disclosure thus rests on the concept that the aging of the conductive track 2 can be controlled deterministically by combining various polymeric coatings with known degradation rates under known aging factors for textile fibres. The destruction of the conductive track 2 and associated break of conductivity is controlled by the degradation of the sacrificial polymeric layers 4 that are sensitive to either UV radiation (Type I sensor), thermal (Type II sensor), or hydrolytic (Type III sensor) aging. When the sacrificial polymer layer 4 is degraded, it cracks and breaks apart. This either disrupts the physical integrity of the conductive track 2, which experiences a reduction in conductivity, or it leaves the conductive track exposed to abrasion associated with normal use of the textile product.

FIGS. 2A to 2E shows one possible configuration of the conductive tracks 2, sacrificial material 4 and substrate materials 6. In this example, the sensor elements 10, that is, the conductive tracks 2 and the sacrificial polymeric materials 4, are placed concentrically around individual fibres 6a of the fabric substrate 6. In other embodiments, the sensor elements 10 may be placed across a fabric or substrate 6 surface. It should be noted that while FIGS. 2A to 2E show the conductive tracks 2 and sacrificial polymeric materials as separate layers, the present disclosure also includes an embodiment of the conductive track 2 and the sacrificial polymer 4 being combined within a single layer 2/4 that is both conductive and sacrificial. In such cases, the single layer 2/4 that is both conductive and sacrificial can be made from an intrinsically conductive polymer, or from a polymer made conductive using conductive additives such as carbon or metal particles.

It is important to note that fabrics are subject to frequent machine washing, which can significantly increase the possibility of abrasion-induced degradation of the sacrificial polymeric layers. Preliminary experiments have confirmed that the RGO coating on meta-aramid fabrics is robust under 10 accelerated washing cycles.

Figure 2:
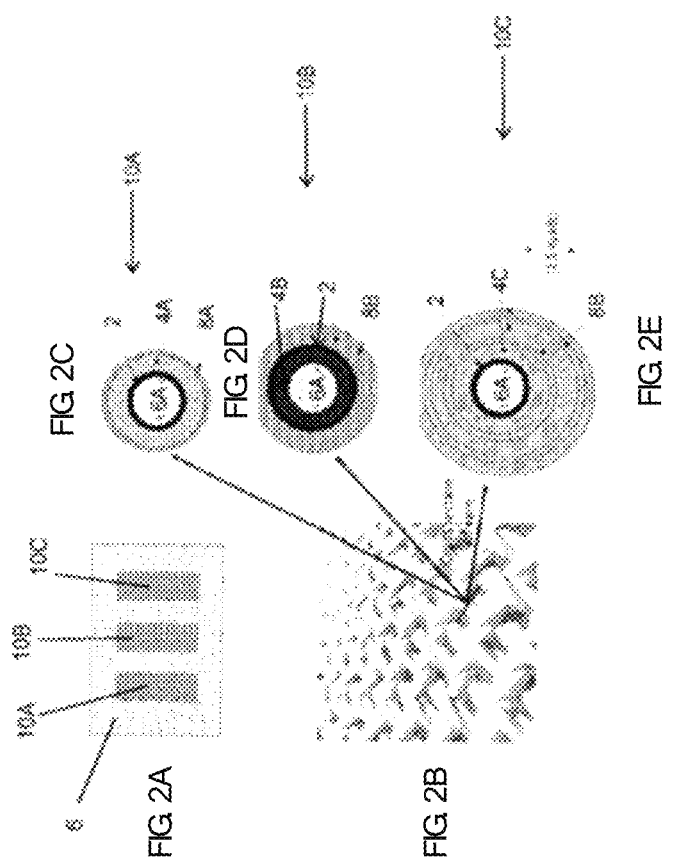
FIG. 2A is a plan view of one embodiment of a sensor assembly of the present disclosure.
FIG. 2B is a perspective view of fibres of a fabric substrate of the sensor assembly of FIG. 2A.
FIG. 2C is a cross sectional view of a substrate fibre wrapped for a UV-aging sensor.
FIG. 2D is a cross-sectional view of a substrate fibre wrapped for a thermal aging sensor.
FIG. 2E is a cross sectional view of a substrate fibre wrapped for a moisture gaining sensor.

In one embodiment, a Type I sensor 10A, which reports on UV aging, comprises a conductive graphene layer 2 deposited on the fabric substrate 6 (FIG. 2C). Then a layer of UV-sensitive polymer 4A such as water-resistant polyurethane (PU) is coated on the graphene layer 2. The UV-induced aging behavior of thermoset PU elastomers is known and has been quantified. Phenolic triazine resins and epoxy resins may also be employed as the UV-sensitive polymer 4A. It is also possible to use polymer composite materials in which the UV degradation is initiated or accelerated by photoactive additives such as Fe- and Ca-stearates, acetophenone/benzophenone, anatase and rutile titanium dioxide nanoparticles, carbon black, hydroxybenzophenone/hydroxyphenylbenzotriazole. Upon degradation of the UV-sensitive polymer layer 4A, the environmental exposure of the graphene layer 2 leads to a UV-induced loss of electrical conduction. The response rate of the Type I sensor 10A may optionally be tuned to match a safety-factor-adjusted UV degradation rate of a specific fabric using a thin protective layer 8A of a wavelength-shifting polymer to protect the sacrificial polymer layer 4A from water if the UV sacrificial polymer 4A is not water resistant. For the purposes of the present disclosure, "safety-factor-adjusted" means that the rate of degradation of the polymer layer is faster than that of the fabric, by a safety factor.

Preferably, laundering durability and decoupling of the effect of other aging factors may be provided by the application of a protective top layer(s) 8. When establishing the laundering durability and the insensitivity to moisture-induced aging in Type I sensors 10A, two aspects must be considered. Firstly, the protective layer 8A should not completely block UV light. Secondly, if the protective layer 8A is hydrophobic, moisture-induced aging can be substantially eliminated. Laundering durability may be provided with optically transparent materials, such as grafting fluoroacrylate polymers, growing silicone nanofilaments, dip-coating epoxy/silica composites or atomic layer deposition (ALD) of thin film oxides as the protective layer 8A. Although these materials are typically not intrinsically transparent to UV light, limiting the coating thickness of the protective layer 8A to submicron level will allow a regulated amount of UV transmission to the UV-sensitive polymer layer 4A. In short, there are many available technological selections for such protective layer 8A.

The effect of thermal aging is, however, difficult to decouple. In some embodiments, the effect of thermal aging may be accounted for with empirical evidence that the degradation of the Type I sensor 10A is predominantly UV-induced in various storage conditions for the fire protective garments.

Type II sensors 10B as shown in FIG. 2D, which target thermal aging, employ a layer of thermally sensitive polymer 4B, e.g. polyetherimide (PEI) and thermoplastic elastomers, on top of the fabric substrate 6. PEI is a thermoplastic polymer with excellent mechanical and high temperature resistance properties. Some heat-resistant thermoplastic elastomers can withstand continuous operation temperatures of ~190° C., which is 0-120° C. below the thermal index of fire-protective fabrics. The conductive graphene layer 2 is deposited on top of the thermally-sensitive polymer layer 4B, whose aging behavior can be predicted by time-temperature superposition. The thermal aging-induced cracking or flow of the polymer layer 4B underneath the graphene layer 2 will result in damage to the graphene layer 2, leading to a reduction or loss of electrical conductivity. The coating thickness of the thermally-sensitive polymer layer 4B will control the sensor response rate.

Durability against laundering, moisture uptake, and UV aging is a challenge when preparing a sensor 10B with decoupled thermal aging. However, compared to the decoupling of the Type I sensor 10A, the Type II sensor 10B enjoys a wider selection of protective coating 8B technologies because optical transparency is not required. Therefore, the thickness of the hydrophobic and laundering-resistant protective layer coatings 8B can be increased to achieve greater protection. Moreover, established yet optically-opaque coatings, such as a thick layer of a room-temperature-vulcanized (RTV) silicone containing a trace amount of reduced graphene oxide, which has been shown to resist over 150 machine washing cycles, may also be included in the selection of the protective layer 8B.

Type III sensor 10C, designed to be moisture-sensitive, may be constructed with the same layout as the Type I sensor 10A, except that a moisture sensitive polymer 4C such as polyimide, para-aramid or polyester-based thermoplastic urethane (TPU) is used as the sacrificial polymeric layer 4C (FIG. 2E). The hydrolysis behavior of these polymers is well-established thus the coating thickness will control the response rate of the sensor 10C. If an increasing thickness is not enough to establish the time span required for assessing long term aging, applying alternating dyads of moisture-sensitive polymer 4C and thin inorganic barrier layers 8C can provide a solution. The thin inorganic layer 8C may comprise non-toxic metals or metal oxides such as aluminum and alumina, produced by a thin film deposition method, such as atomic layer deposition (ALD).

While the above description focuses on UV, moisture and thermal aging, it would be understood by a person of skill in the art that other aging conditions for which sensors can be made in a similar format include but are not limited to chemical exposure, degradation by chemicals (e.g. acids, n-alkalis, various organic solvents, bleach (aramids are sensitive to bleach), mold or mildew, degradation by biological agents (bacteria, fungi), laundering, abrasion, and smoke exposure.

Figure 3:
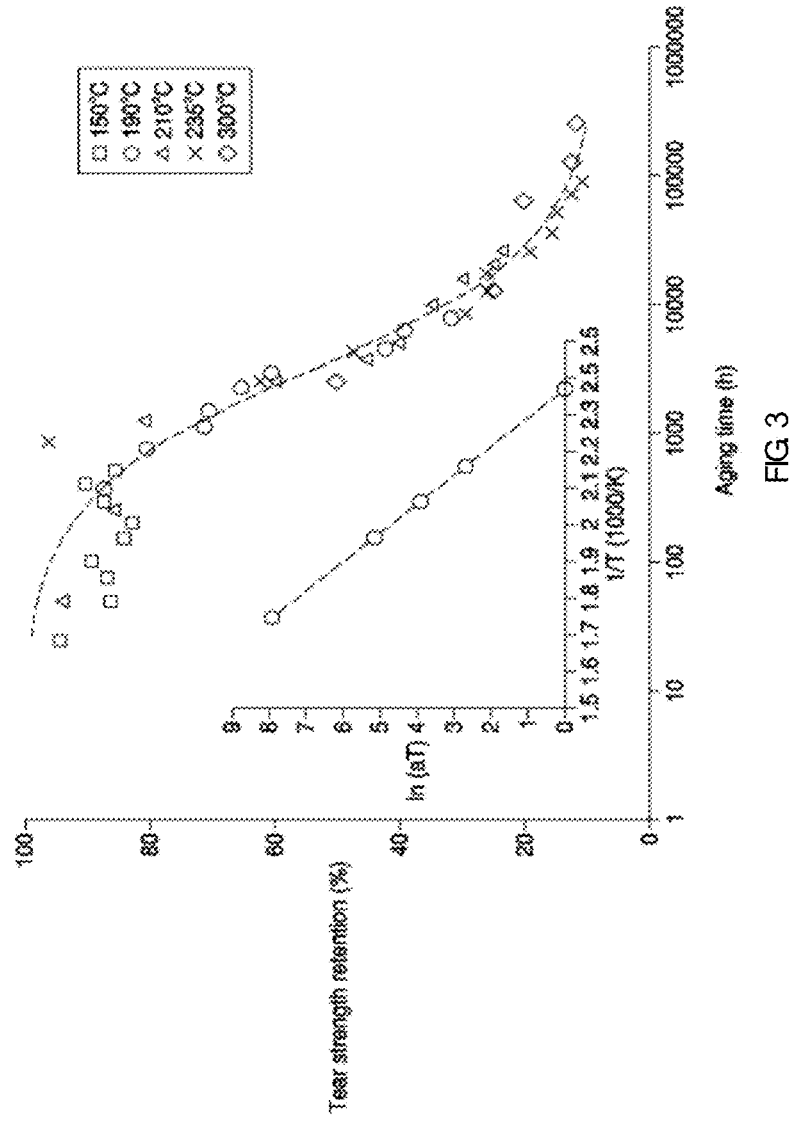
FIG. 3 is a graph of tear strength retention in % vs. aging time in hours at various temperatures and fitted with a 3-parameter Hill equation, for a 60% Kevlar™/40% Basofil™ fabric.

Analysis of the aging performance of the sensors is conducted using models developed to describe the effect of aging on the performance of fire protective fabrics. For instance, the effect of thermal aging on the tear strength of fabrics used as the outer shell of protective garments exposed to heat and flame has been successfully described using the Arrhenius equation for the temperature variation and the 3-parameter Hill equation for the time variation (FIG. 3).

In the case of hydrolytic aging, a kinetic model developed for the aging of a Kevlar®/PBI blend fabric involves two competing reactions taking place simultaneously: the hydrolysis of the Kevlar amine bond and a recombination reaction. The combined thermal, photochemical and hydrolytic aging simulated by exposing fabrics to alternating cycles of UV and 100% relative humidity (RH) at 50° C. or 60° C. was satisfactorily described by the following equation:

$$t_L = A \times I^\alpha \left( \frac{E_a}{RT} \right) \times \exp(C \times RH)$$

With tL, being the thermal life; I, the UV intensity; T, the temperature; and RH, the relative humidity.

The UV, thermal and moisture/hydrolytic sensors 10A, 10B and 10C are deposited on the substrate 6 (FIG. 4) to form a sensor patch 100. It is also possible to apply only one or only two sensor types 10 to a particular substrate 6 to form a single or double sensor patch 100. The sensor assembly can then be attached at strategic locations on the protective garment. A preferred material for the substrate 6 is a fabric, although the substrate 6 could also be a polymer film or even a metal strip. The substrate material should be able to resist ageing under conditions that are damaging for the protective garment fabric, the condition of which is being monitored by the sensors 10, such that there is no unwanted substrate degradation that could interfere with sensor operation. The substrate 6 should also be able to withstand the same laundering conditions as the fabric to which it is applied. It should have excellent mechanical flexibility so that it does not affect the flexibility of the garment or other textile product on which it is fixed. It must be able to be attached, for instance by sewing, to the fabric of the garment or textile product. Finally, the substrate 6 should be such that it allows for good quality coating by the conductive tracks 2 and sacrificial polymers 4. A preferred embodiment as a sensor substrate 6 for application to fire-protective clothing is a 93% meta-aramid/5% para-aramid/2% anti-static fibre blend woven fabric.

Examples—the following examples are provided to exemplify the described disclosure, and not to limit the claimed disclosure in any manner.

Example 1—Type II Sensor

Figures 4, 5A, 5B:
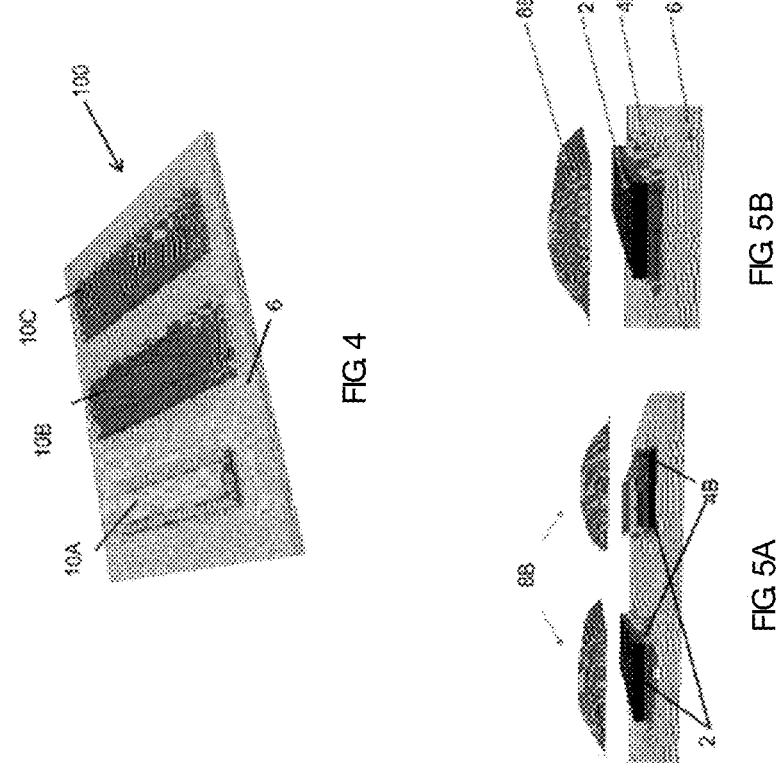
FIG. 4 is a perspective view of an embodiment of a sensor assembly of the present disclosure.
FIG. 5A is a perspective view showing two possible embodiments of a thermal-aging sensor of the present disclosure.
FIG. 5B is a close up perspective view of one of the embodiments of FIG. 5A.

An exemplary Type II sensor 10B can consist of a polyetherimide (PEI) film as the thermally sensitive polymer layer 4B, a conductive laser-induced-graphene (LIG) layer as the conductive track layer 2, and a fabric substrate layer 6. The conductive track layer can be positioned above or below the thermally-sensitive polymer layer, as illustrated in FIG. 5A.

In this design, the PEI film is a sensing layer 4B that mimics the thermal aging of fire protective clothing. The conductive layer 2, which is patterned by LIG technique on the PEI film, can be monitored electronically. As the PEI film layer 4B undergoes thermal aging, microcracks result, and the LIG conductive layer 2 will be affected by these microcracks. Thus, the electrical conductivity of the LIG layer 2 will change as the PEI film layer 4B is thermally aged. Conductive RGO coatings on fabrics can also be used to create the conductive layer 2, for example for e-textile applications, and have high stability under mechanical deformation; the thermal aging of PEI will track the thermal aging of fire protective clothing. The aging process will be reflected by the changing electrical conductivity of the LIG layer 2. Therefore, PEI-LIG thermal aging sensors 10B will offer a simple reading of electrical conductivity changes as the thermal aging progresses in fire protective clothing. The electrical resistance change will inform the aging status of the fire protective clothing and give an indication of when the fire protective clothing needs to be replaced. This sensor 10B will be a useful tool to estimate the lifetime of garments in special field applications, such as, aerospace, or military fields.

To prepare a laser-induced-Graphene (LIG) layer 2 on the polyetherimide film 4B, a 250 μm thick polyetherimide (PEI) film was purchased from McMaster Carr and placed in a 70 W 10.6 μm laser scribing system 12 (PLS 6.150 D, Universal Laser System, Inc) equipped with a CO2 laser for patterning. During patterning of the graphitic layer 2 on the PEI layer 4B, the speed and power were set to 5% for patterning and 10% for cutting, respectively. The pulses per inch value was fixed at 500 during the engraving processes. The LIG layer 2 formation on the PEI film 4B is illustrated in FIG. 6.

Figures 6, 7A, 7B, 7C, 7D:
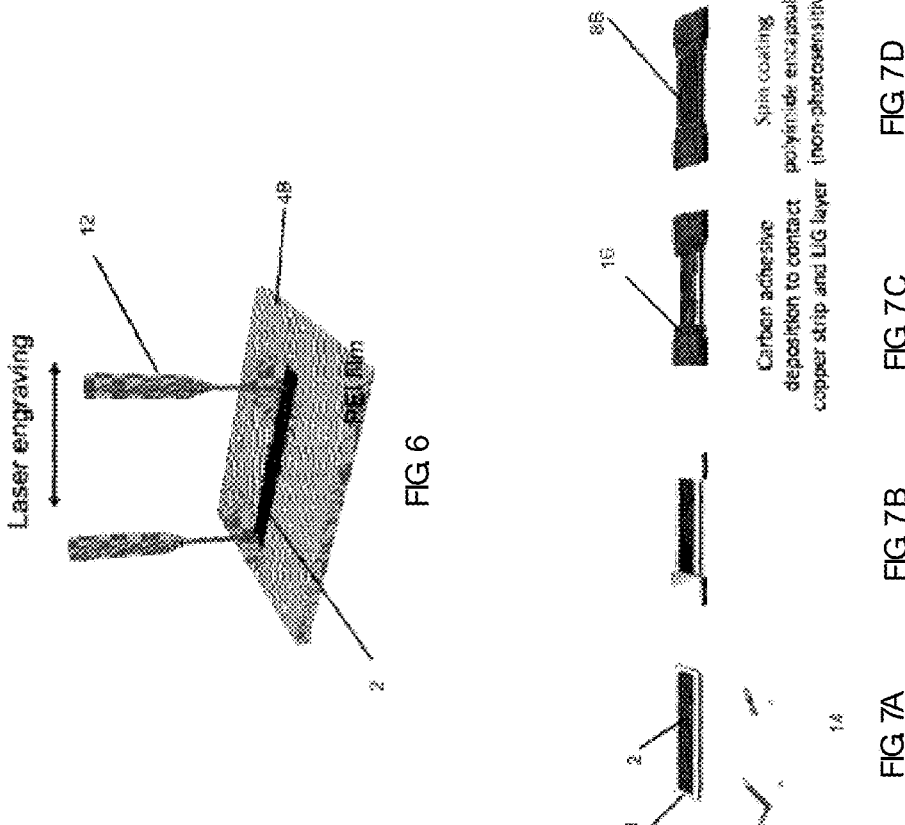
FIG. 6 is a perspective view of one embodiment of applying a graphene layer to a substrate by laser patterning.
FIG. 7A to 7D illustrate the steps of one embodiment of manufacturing a thermal-aging sensor of the present disclosure.

In order to read the electrical resistance of a LIG layer 2 on a PEI film 4B, electrical connections were made by bonding copper strips 14 to the LIG layer 2, as illustrated in FIGS. 7A and 7B. A carbon adhesive 16 (DAG-T-502, Ted Pella, CA, USA) was used both to bond the copper strip 14 to the LIG layer 2, and as a protective layer on top of the copper strip 14 (after bonding) for prevention of oxidation during thermal aging, as illustrated in FIG. 7C. In the last step, a non-photosensitive polyimide encapsulant (PI 2574, HD MicroSystems, NJ, USA) was encapsulated on the LIG layer by application by spin coater (Laurell Model WS-650MZ-23NPP) at 1000 rpm for 1 min, as illustrated in FIG. 7D, the non-photosensitive polyimide encapsulant serves as the protective layer 8B.

The PEI-LIG sensor was thermally aged using two methods. First, the fabricated PEI-LIG sensor was placed in a convection oven (Model 281 A Vacuum Oven, Fisher Scientific) set to a temperature of 270° C. In order to observe resistance changes at different aging times, 6 groups were prepared (each group contains 5 samples) and each group was aged a different time (4 days for Group 1, 10 days for Group 2, 14 days for Group 3, 21 days for Group 4, and 28 days for Group 5). The resistance was measured for each group after different aging time intervals and then the samples were placed back into the oven between measurements until a total time span of 4 weeks was reached. For Group 1, the sensors measured after 4, 10, 14, 21, and 28 days. For Group 2, the sensors measured after 10, 14, 21, and 28 days. For Group 3, the sensors measured after 14, 21 and 28 days. For Group 4, the sensors measure after 21 and 28 days. The electrical resistance of the sensors at the desired time points was measured by a Bench LCR meter (BK precision model 895, CA) by clipping with alligator clips.

In the second set of experiments, PEI-LIG sensors were placed on a hot plate and thermally aged at 210° C., 250° C., 260° C., 270°, and 280° C. for 80 h, and the electrical resistance of the sensors was measured using the same method as above.

An accelerated laundering test was conducted to assess the effect of repeated laundering on the electrical conductivity of the LIG layer on the PEI layer. Samples were encapsulated with a polyimide encapsulant (HD Microsystems, NJ) and cured at 180° C. for 2 hrs, and then left at room temperature for 48 hours. Accelerated washing was performed with a Launder-Ometer (Atlas, IL, USA) following the ISO 105-C06 standard and test procedure A1S. One accelerated washing cycle in the Launder-Ometer is equivalent to 1 cycle of domestic laundering. According to this standard, 150 ml of washing solution prepared with 4 g/L of detergent was used to wash the sensors with 10 steel balls at 40° C. Four canisters of 5 sensors were prepared. Five sensors were collected from the canister after a predetermined number of washing cycles (1, 3, 5, and 10 cycles), where each cycle lasted 6 min. Immediately after being collected, the specimens were rinsed with DI water and dried at room temperature for 24 hours. Then, the electrical resistance of each of the five sensors was measured.

Depending on the test, between three and five replicates of the sensors were tested. Average values and standard errors of the electrical resistance measurements are reported. Where applicable, statistical significance was evaluated using the single factor ANOVA analysis. A confidence level of 0.05 was set to establish significance.

In order to assess the long-term thermal aging of the sensors, five groups of five sensors were placed in a convection oven at 270° C. All five groups have a total aging time of 28 days (672 hours), but each group has a distinct thermal history. The black solid line in FIG. 8 follows the evolution of the average resistance values for Group 1, 2, 3, 4, and 5 sensors, which have undergone uninterrupted annealing times of 4, 10, 14, 21, and 28 days, respectively. The uninterrupted thermal aging resulted in an increase of the normalized resistance values by 1.65, 3.24, 3.76, 6.79, and 10.6 times for Group 1, 2, 3, 4, and 5 sensors, respectively.

Figure 8:
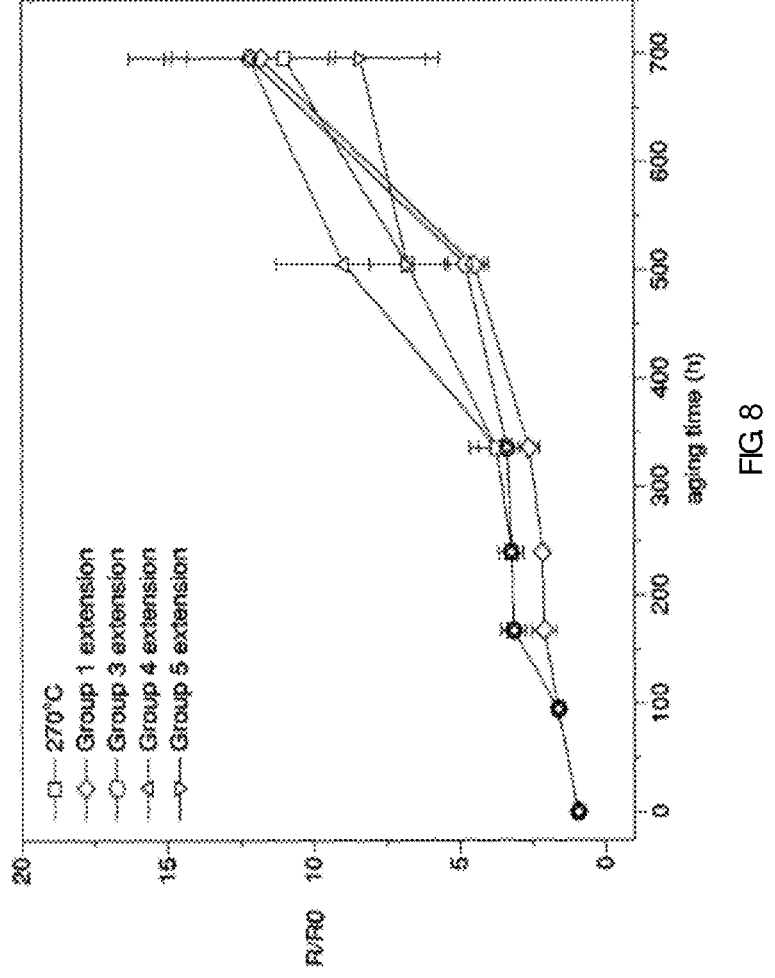
FIG. 8 is a graph of electrical resistance change over aging time of a PEI-LIG thermal-aging sensor at 270° C. for 4 weeks.

The effect of intermittent cooling to room temperature was studied by putting Group 1, 2, 3 and 4 sensors back in the oven after being measured; these samples were exposed to cooling/measuring/heating cycles periodically up until 28 days. When comparing the mean values of resistance at each aging condition (FIG. 8), the resistance is increased over the annealing time in both uninterrupted/interrupted annealing. FIG. 8 shows resistance changes after accelerated thermal aging of PEI-LIG sensors at 270° C. for 4 weeks. The black line indicates the average values for each group at the designate time point (e.g. Group 1 at 4 days, Group 2 at 10 days, etc.). The various dashed lines track each group after their initial designated time point as their aging was extended their aging to 4 weeks. A statistical analysis was conducted between the different aging conditions and shows no statistically significant difference in resistance between the results for the different sensor Groups. Therefore, subjecting the sensors to intermittent cooling does not seem to affect their overall thermal aging behavior in terms of electrical conductivity.

The short-term aging experiment involved placing five groups of sensors on a hotplate; each group has three sensors. Each group of sensors was exposed to thermal aging on the hotplate for 80 h at a different temperature (210, 250, 260, 270 and 280° C.). The temperature of 210° C. was chosen to determine how the resistance changed at a temperature lower than the glass transition temperature (Tg) of 215° C. of PEI [65]. All the other temperatures selected were above Tg; such high temperatures are often experienced by firefighters in operation.

Figure 9:
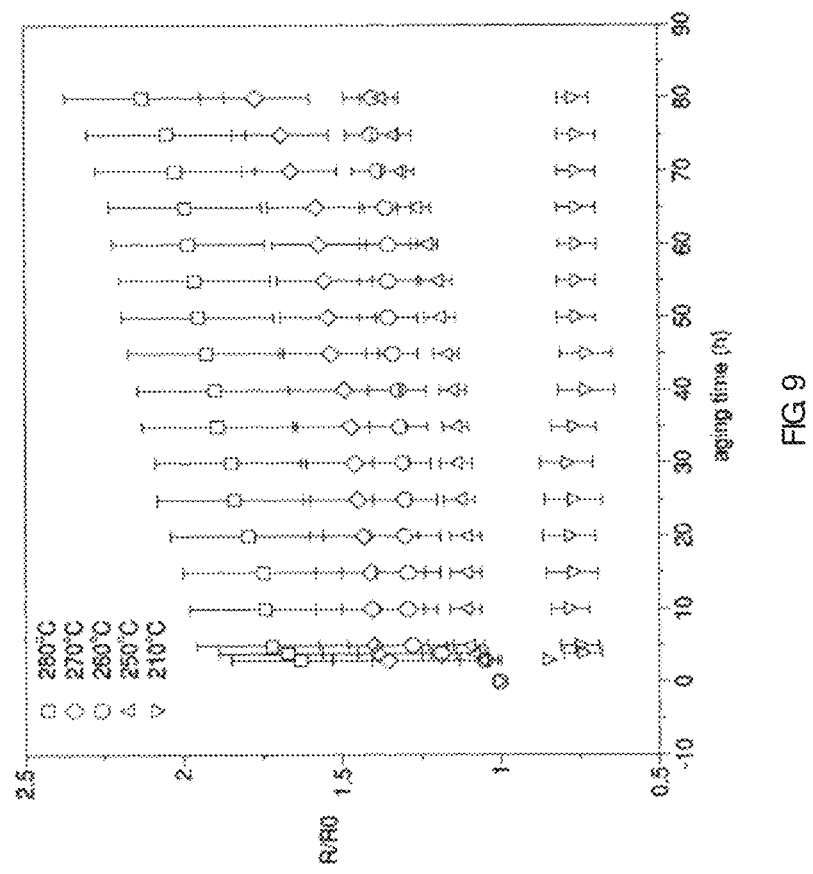
FIG. 9 is a graph of the change in normalized electrical resistance values of a PEI LIG thermal aging sensor at different temperatures.

FIG. 9 shows the change in the average normalized resistance of each group of sensors exposed to different temperatures for 80 h. The resistance of the sensors exposed to an aging temperature below the Tg decreased after aging. This drop in resistance may be attributed to a contact annealing effect between the copper strips and the LIG layer. At temperatures higher than Tg, the resistance values increased consistently with time; the level of increase became larger as the temperature increased from 250° C. to 280° C. It is notable that the change in resistance observed after 80 h of aging at 270° C. in the short-term aging experiment on a hot plate (/0=1.77; FIG. 9) is similar to the value obtained after 100 h at the same temperature in the long-term aging experiment in a convection oven (/0=1.65; FIG. 8).

Figure 10:
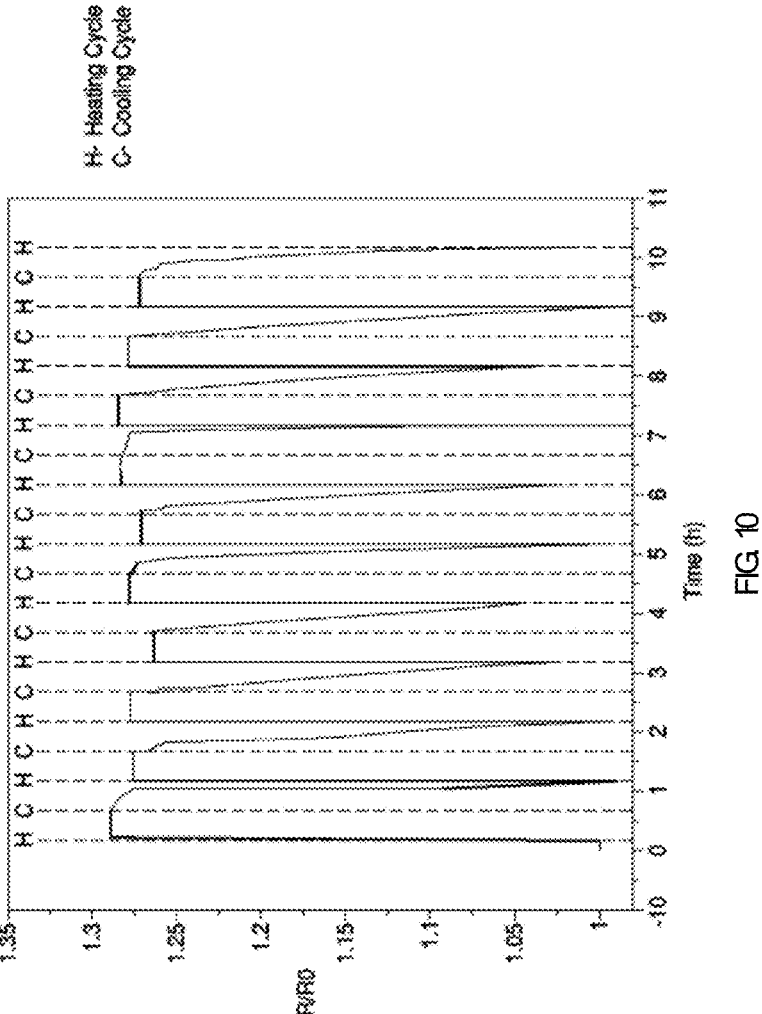
FIG. 10 is a graph of normalized electrical resistance over time for ten heating/cooling cycles of a PEI-LIG thermal aging sensor, wherein each cycle comprised 0.5 hours of heating and 0.5 hours of cooling.

The thermal stability of the sensor was investigated by subjecting the PEI-LIG sensors to heating/cooling cycles. When firefighters are working near a fire, the high temperature exposure is often brief, followed by a cool down in ambient air. In order to verify the reproducibility of the resistance values over several heating/cooling cycles, a PEI-LIG sensor was exposed to repeated cycles of heating at 270° C. for 30 min and subsequent cooling in ambient air for 30 min, as shown in FIG. 10. The results are expressed in terms of the change in the normalized resistance R/R0. The normalized resistance values reached a steady state quickly upon heating.

Figure 11:
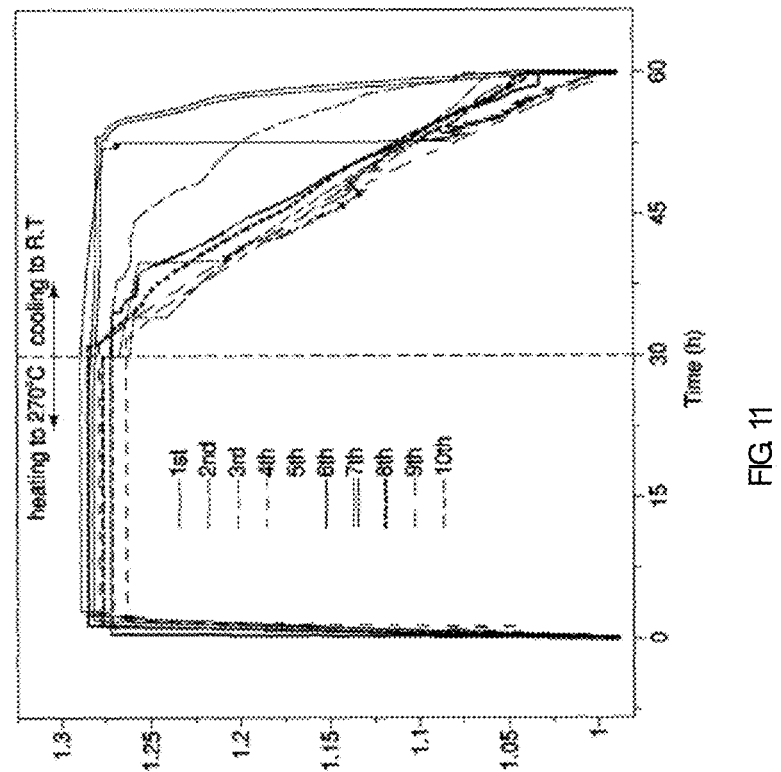
FIG. 11 is a graph of normalized electrical resistance over time for a PEI-LIG thermal aging sensor for 10 cycles of heating to 270° C. and cooling to room temperature.

However, there were noticeable delays between the start of the cooling and the drop observed in the resistance. In FIG. 11, the transient curves showed that, out of 10 cooling cycles, six cycles showed fairly consistent cooling rates whereas four cycles show some scattering in the cooling trend. A possible explanation of this lack of consistency in the cooling curves is a non-uniform airflow in the lab during the cooling phase, which took place under uncontrolled cooling conditions. However, a promising result from the experiment is that the steady-state normalized resistance values at 270° C. are highly consistent at R/R0=1.28±0.02 over 10 cycles.

If the end-of-life sensor is integrated in a garment, one of the biggest challenges is related to launderability. During the laundering, the mechanical stresses applied to a sensor may affect its electrical components [67]. The conditions that a garment experiences during laundering also include elevated temperature, exposure to chemicals, and high moisture environment. These conditions can easily affect the functionality of textile-based sensors in an adverse manner. Therefore, it is important to encapsulate the sensor with a protective layer to avoid possible damage during laundering; in the current study, the PEI-LIG sensor was encapsulated with a polyimide layer.

Figure 12:
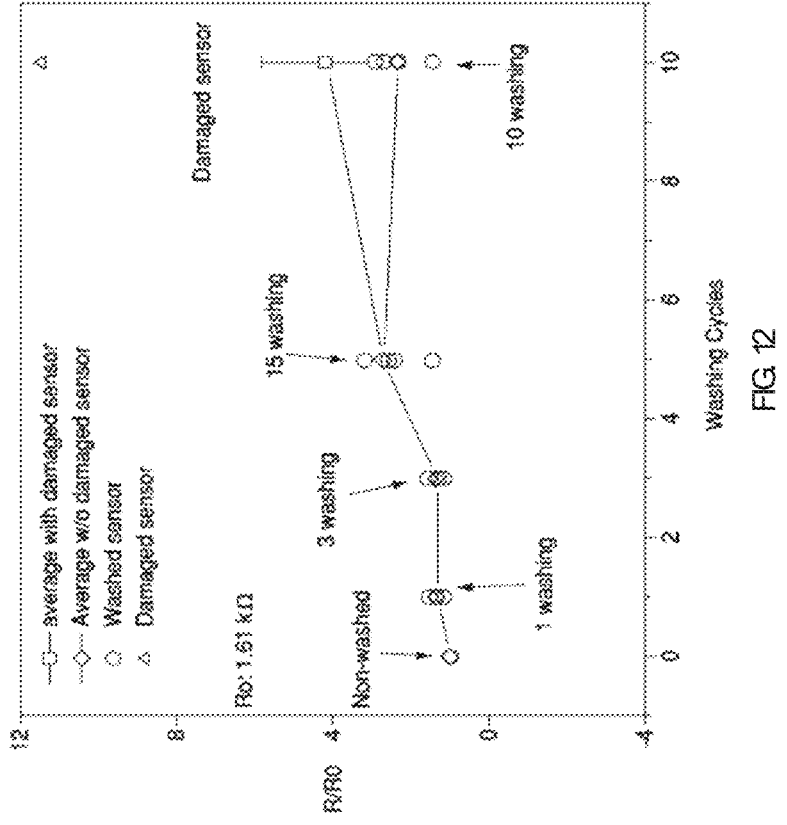
FIG. 12 is a graph of normalized electrical resistance over washing cycles for a PEI LIG thermal aging sensor.

The stability of the PEI-LIG sensors under laundering was assessed by measuring their electrical resistance after selected numbers of washing cycles. In FIG. 12, the average normalized resistance of the encapsulated PEI-LIG sensors is plotted as a function of the washing cycles experienced. Their average resistance was 1.6±0.6 kΩ before washing and it increased when they were subjected to laundering cycles. Normalized resistance values, R/R0 of 1.30, 1.34, and 2.72 were obtained after 1, 3, and 5 cycles, respectively. After 10 cycles, one of the five sensors in the batch was severely damaged, showing an individual R/R0 value of 11.5. The average normalized resistance was 2.33 when excluding the damaged sensor and 4.16 if it was included. The images of the PEG-LIG sensors inserted in FIG. 12 illustrate the typical damages observed on the sensors after the repeated laundering cycles.

A single factor ANOVA analysis excluding the damaged sensor was performed. It indicates that at least one of the washing conditions is different from the other washing conditions (It is noted that the p-value becomes 0.12 (n=25) when the damaged sensor is included, which supports the null hypothesis of 'no difference'; however, this result can be attributed to anomalously large sample variance of the group of sensors subjected to 10 washing cycles, and thus the interpretation seems more reasonable by excluding the outlier). We thus concluded that a significant change in resistance is produced when the sensors are subjected to 10 repeated washing cycles.

Example 2—Substrate Fabric for the End-of-Life Sensor

A series of fabrics were investigated as potential substrate for the end of life sensor. They included blends of meta- and para-aramid, polybenzimidazole (PBI) and polybenzoxazole (PBO) fibres as well as fabrics composed of glass, cotton, regenerated cellulosic fibres, nylon, polyester, oxidized polyacrylonitrile (PAN), modacrylic, and novoloid fibres. All of the selected fabrics are either inherently flame resistant (FR) or treated to be FR.

The fabrics were subjected to accelerated ageing conditions selected to simulate conditions that are encountered by firefighters while on duty. The purpose of this assessment was to identify the fabrics that can resist ageing conditions that are known to be damaging to the fire-resistant clothing to ensure that the sensor fabric substrate does not interfere with the operation of the sensor over the life of the garment. The criterion used to determine the accelerated ageing conditions for the fabric assessment was the point at which the performance of the outer shell fabric reaches the minimum strength requirement established in NFPA 1971 (2018) for structural firefighting and proximity firefighting protective ensembles when exposed to the accelerated ageing conditions. These ageing conditions, shown in Table 1, were determined using data available in the literature where researchers investigated the effect of different accelerated ageing conditions on the mechanical performance of fire protective fabrics used as outer shell of firefighters' clothing.

TABLE 1

| List of accelerated ageing conditions. | |
| --- | --- |
| Accelerated aging Test | Conditions |
| UV | 243 h, 1 W/m² @ 340 nm, 80° C. |
| Thermal | 42 h, 235° C. |
| Laundering (laundero-meter) | 10 cycles; washing: 45 min, 60° C., flat drying |
| Hydrothermal | 15, 24 and 31 days, 80° C. |

The best performing fabric is made of Nomex IIIA (93% meta-aramid fibres, 5% para-aramid fibres, 2% carbon fibres). It showed a 25% loss in tear strength after thermal ageing. It was considered good when compared to other fabrics currently used as the outer shell of firefighters' clothing, which lost between 70 and 90% of their strength after exposure to the thermal aging conditions. The tear strength of the fabric was not affected by the hydrothermal aging or accelerated laundering. On the other hand, it was strongly affected by UV irradiation and lost 70% of its mechanical strength, which can be explained by the high sensitivity of aramid fibres to UV light. However, the fabric could be protected against the effects of UV radiation by a surface treatment using UV blockers or absorbers such as carbon black or titanium dioxide nanoparticles.

A narrow width fabric was subsequently manufactured using a 28/2Ne Vortex spun (Staple spun, 2-ply, S-Z twist) Nomex IIIA yarn. The fabric.structure is 2:1 basket weave. The fabric count is 30 ends/cm and 22 picks/cm for a total of 52 yarns/cm². The unit mass is 238 g/m² and the thickness is 0.57 mm.

Example 3—Sacrificial Polymer for Type III Sensor

Polyimides combine mechanical toughness and chemical and thermal resistance with a low dielectric constant and thermal expansion coefficient. Aromatic polyimides can operate in a very wide range of temperatures. For instance, Kapton®, which was developed by DuPont, has been successfully used at temperatures as low as −269° C. and as high as 400° C.

On the other hand, polyimides are sensitive to moisture. They can absorb up to 3 wt % of water from atmospheric humidity, which can lead to an increase in dielectric permittivity, a decrease in electrical resistivity, and mechanical failure.

A polyimide film was aged by immersion in reverse-osmosis (RO) water. Specimens were suspended inside a jar and stored in an oven at temperatures of 70, 80, and 90° C. for up to 56 days. Aged samples were collected at regular intervals and the residual ultimate tensile strength (UTS) and elongation at break were measured.

Figure 13:
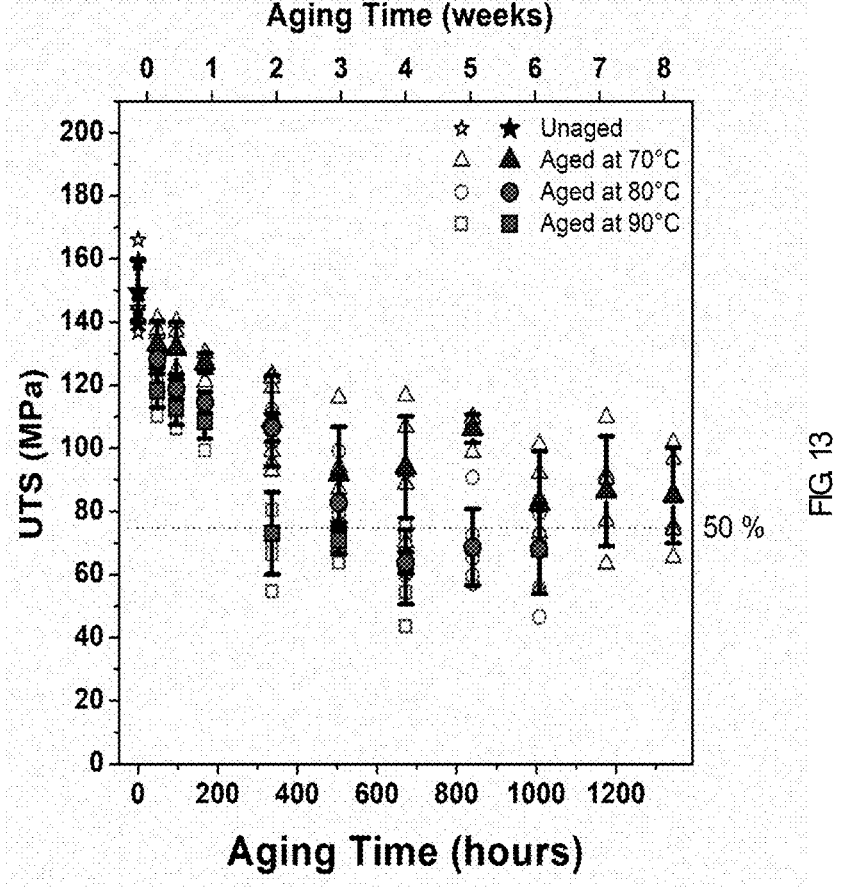
FIG. 13 is a graph of variation of the UTS of unaged and hydrothermally aged polyimide film specimens as a function of aging time.

A decrease in the UTS (FIG. 13) and elongation at break (FIG. 14) is observed for all three aging temperatures. This decrease occurred faster when the aging temperature was higher. The UTS decreased from 150 to 64 MPa after 4 weeks of hydrothermal aging at 90° C. This corresponds to a 43% decrease in the UTS of the polyimide film. FIG. 13

Figure 14:
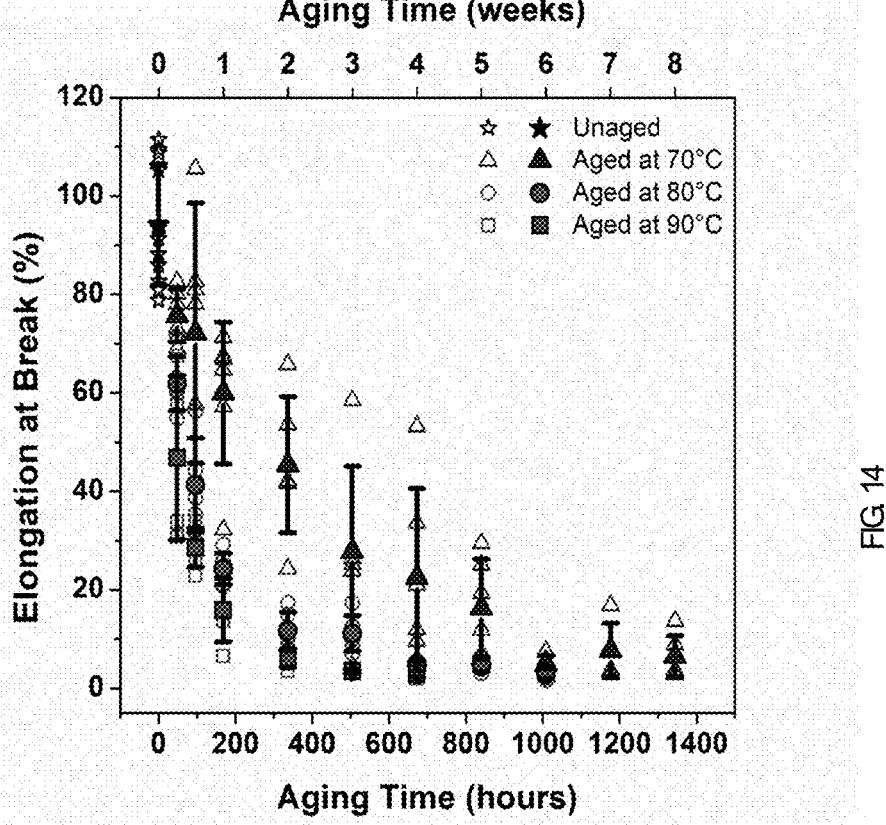
FIG. 14 is a graph of variation of the elongation at break of unaged and hydrothermally aged polyimide film specimens as a function of aging time.

13 is variation of the UTS of unaged and hydrothermally aged polyimide film specimens as a function of aging time. (Hydrothermal Aging of Polyimide Film Braun C, Nam S L, de la Mata P A, Harynuk J J, Chung H-J, Dolez P I. J App Polym Sci. 2022; e52183. (11p) https://doi.org/10.1002/app.52183). FIG. 14 is variation of the elongation at break of unaged and hydrothermally aged polyimide film specimens as a function of aging time. (Hydrothermal Aging of Polyimide Film Braun C, Nam S L, de la Mata P A, Harynuk J J, Chung H-J, Dolez P I. J App Polym Sci. 2022; e52183. (11p) https://doi.org/10.1002/app.52183).

Figure 15:
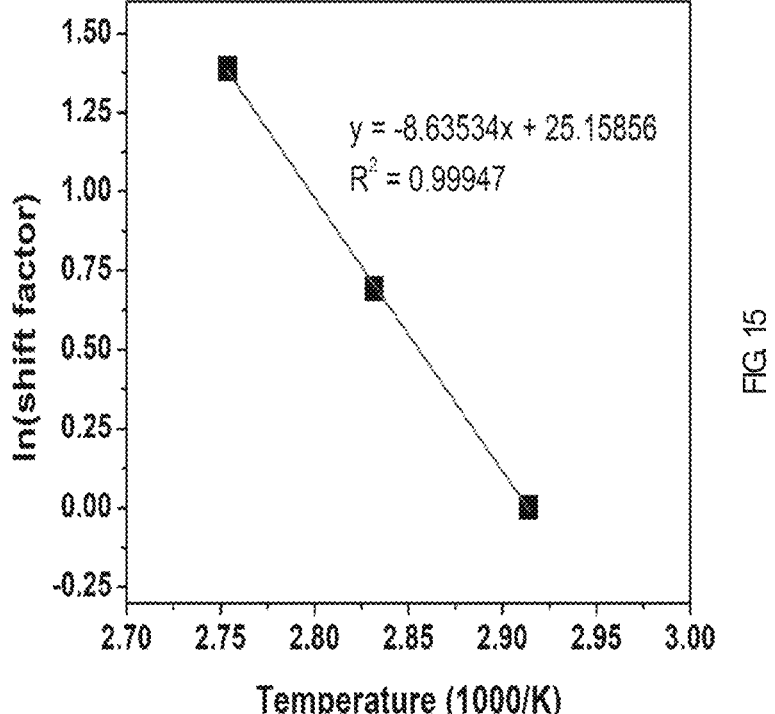
FIG. 15 is an Arrhenius plot for the effect of hydrothermal aging on the UTS of the polyimide film.

The activation energy corresponding to the effect of hydrothermal aging on the tensile strength of the polyimide film was calculated from an Arrhenius plot constructed using the UTS data. The time-temperature principle was used to obtain the shift factors in the Arrhenius plot (FIG. 15). The slope of the Arrhenius plot provides an activation energy for the hydrothermal aging of polyimide 71.8±0.1 kJ/mol.

This value is similar to the activation energies of 53 to 65 kJ/mol reported for Kevlar®/PBI blend fabrics subjected to hydrothermal aging between 6° and 90° C. and assessed in terms of breaking force retention. This suggests that this polyimide film could be used as the sacrificial polymer for the Type III moisture end-of-life sensor for fire-protective fabrics. FIG. 15 is an Arrhenius plot for the effect of hydrothermal aging on the UTS of the polyimide film. (Hydrothermal Aging of Polyimide Film Braun C, Nam S L, de la Mata P A, Harynuk J J, Chung H-J, Dolez P I. J App Polym Sci. 2022; e52183. (11p) https://doi.org/10.1002/app.52183)

Interpretation.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the disclosure.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The invention claimed is:
1. A sensor for measuring the degradation of a fabric property of a fabric, comprising:
  (a) a conductive track; and
  (b) a sacrificial material coupled to the conductive track, said sacrificial material being sensitive to at least one aging condition of the fabric, such that degradation of the sacrificial material results in reduction or loss of electrical conductivity of the conductive track,
wherein the reduction or loss of electrical conductivity of the conductive track from degradation of the sacrificial material signals degradation of the fabric property.

2. The sensor of claim 1 wherein the fabric is a high-performance fabric.

3. The sensor of claim 2 wherein the fabric property comprises mechanical strength, thermal and/or fire resistance, and wherein the least one aging condition comprises heat, ultraviolet light (UV), and moisture.

4. The sensor of claim 3, wherein the conductive track comprises a carbon-based compound selected from reduced graphene oxide and metal compounds.

5. The sensor of claim 4 wherein the conductive track and the sacrificial material are applied to a substrate to form a sensor patch.

6. The sensor of claim 5, wherein the sacrificial material comprises a UV sensitive polymer coated on the conductive track.

7. The sensor of claim 6 where the UV sensitive polymer comprises polyurethane, phenolic triazine resins or epoxy resins.

8. The sensor of claim 7, wherein the UV sensitive polymer further comprises additives controlling the UV-degradation rate of the polymer.

9. The sensor of claim 8 further comprising a thin covering layer of a wavelength-shifting polymer.

10. The sensor of claim 9 further comprising a protective top layer that is substantially UV light transparent.

11. The sensor of claim 10 wherein the protective layer is also hydrophobic.

12. The sensor of claim 11 wherein the protective layer is composed of fluoroacrylate polymers, silicone nanofilaments, epoxy/silica composites or thin film oxides.

13. The sensor of claim 5, wherein the sacrificial material comprises a thermally sensitive polymer.

14. The sensor of claim 13 wherein the thermally sensitive polymer is comprised of polyetherimide or thermoplastic elastomers.

15. The sensor of claim 14 wherein the thermally sensitive polymer is layered below the conductive track.

16. The sensor of claim 14 wherein the thermally sensitive polymer is layered above the conductive track.

17. The sensor of claim 16 further comprising a protective layer, comprising a moisture protective material.

18. The sensor of claim 17, wherein the protective layer is a room-temperature-vulcanized (RTV) silicone containing a trace amount of reduced graphene oxide.

19. The sensor of claim 5, wherein the sacrificial material comprises a moisture sensitive material.

20. The sensor of claim 19, wherein the moisture sensitive material comprises thermoplastic urethane, para-aramid or polyimide polymer.

21. The sensor of claim 20 wherein the moisture sensitive material is layered with the conductive track in an arrangement selected from the group consisting of below the conductive track and above the conductive track.

22. The sensor of claim 20 comprising repeating layers of the moisture sensitive material and an inorganic material deposited as a thin film.

23. The sensor of claim 22 wherein the inorganic material is a metal or metal oxide.

24. The sensor of claim 23, wherein the conductive track is produced by a reduced graphene oxide wrapping technique, or a laser-induced grafting production technique.

25. The sensor of claim 24, wherein the conductive track and the sacrificial polymer are combined within a single layer that is both conductive and sacrificial.

26. The sensor of claim 25, wherein the single layer that is both conductive and sacrificial is an intrinsically conductive polymer or a polymer made conductive using conductive additives such as carbon or metal particles.

27. The sensor of claim 5, wherein the substrate is made from a material selected from the group consisting of fabrics, polymer films and metal strips.

28. The sensor of claim 27, wherein the substrate material is mechanically flexible to move with the fabric to which it is affixed.

29. The sensor of claim 28, wherein the substrate is a 93% meta-aramid/5% para-aramid/2% anti-static fibre blend woven fabric.

30. A method of measuring the performance degradation of a fabric, using a sensor as claimed in claim 1, comprising the step of measuring the electrical resistance of the sensor, and comparing the result to a known or empirically measured value to estimate the remaining useful life of the fabric performance.

* * * * *